United States Patent
Kroll et al.

(10) Patent No.: US 7,225,030 B2
(45) Date of Patent: May 29, 2007

(54) MANAGEMENT OF IMPLANTABLE DEVICES

(75) Inventors: Mark Kroll, Simi Valley, CA (US); Hans Abrahamson, Stockholm (SE); Magnus Lindberg, Sundyberg (SE); Magnus Öhman, Hässelby (SE); Mats Arturson, Täby (SE)

(73) Assignee: St. Jude Medical AB, Jarfalla (SE)

( * ) Notice: Subject to any disclaimer, the term of this patent is extended or adjusted under 35 U.S.C. 154(b) by 77 days.

(21) Appl. No.: 10/504,895

(22) PCT Filed: Nov. 26, 2002

(86) PCT No.: PCT/SE02/02182

§ 371 (c)(1),
(2), (4) Date: Feb. 15, 2005

(87) PCT Pub. No.: WO03/072192

PCT Pub. Date: Sep. 4, 2003

(65) Prior Publication Data

US 2005/0131492 A1    Jun. 16, 2005

(51) Int. Cl.
*A61N 1/00* (2006.01)

(52) U.S. Cl. .................. 607/60; 607/32; 607/31; 607/59

(58) Field of Classification Search ............... 607/32, 607/60, 2, 31, 59; 600/300; 128/903; 705/2, 705/3
See application file for complete search history.

(56) References Cited

U.S. PATENT DOCUMENTS

| | | | |
|---|---|---|---|
| 6,083,248 A | 7/2000 | Thompson | |
| 6,249,705 B1 | 6/2001 | Snell | |
| 6,292,698 B1 | 9/2001 | Duffin et al. | |
| 6,327,501 B1 | 12/2001 | Levine et al. | |
| 6,347,245 B1 * | 2/2002 | Lee et al. .................. | 600/523 |
| 6,648,823 B2 * | 11/2003 | Thompson .................. | 600/300 |
| 7,076,303 B2 * | 7/2006 | Linberg ....................... | 607/32 |

FOREIGN PATENT DOCUMENTS

| | | |
|---|---|---|
| WO | WO 01/49368 | 7/2001 |
| WO | WO 01/82210 | 11/2001 |

\* cited by examiner

*Primary Examiner*—Robert E. Pezzuto
*Assistant Examiner*—Natasha Patel
(74) *Attorney, Agent, or Firm*—Schiff Hardin LLP

(57) ABSTRACT

In a method and a system for organizing not yet implanted implantable medical devices, each having a telemetry unit associated therewith, a local administration unit transmits an inquiry signal to at least one of the telemetry units and receives a return signal therefrom in response to the inquiry signal. The return signal establishes the existence of the medical device, and the local administration unit, or a remote external unit in communication with the local administration unit, can then determine a course of action to be taken, such as a recall procedure, invoicing or taking inventory, based on the return signal from the medical device.

19 Claims, 2 Drawing Sheets

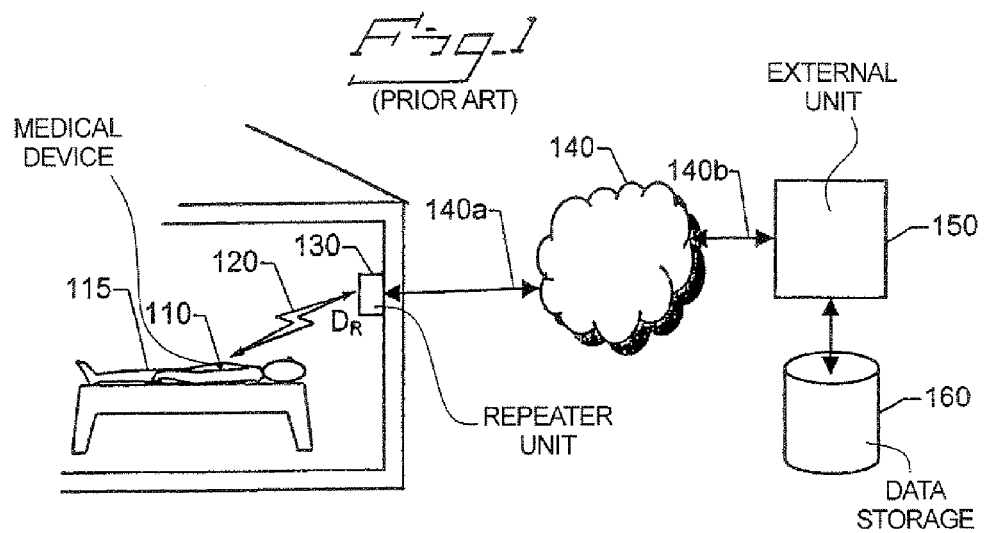
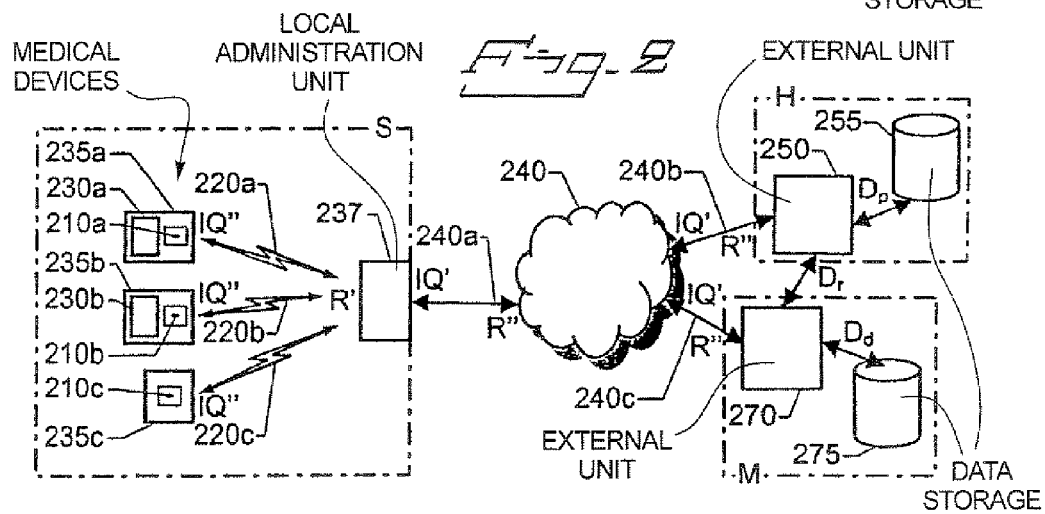
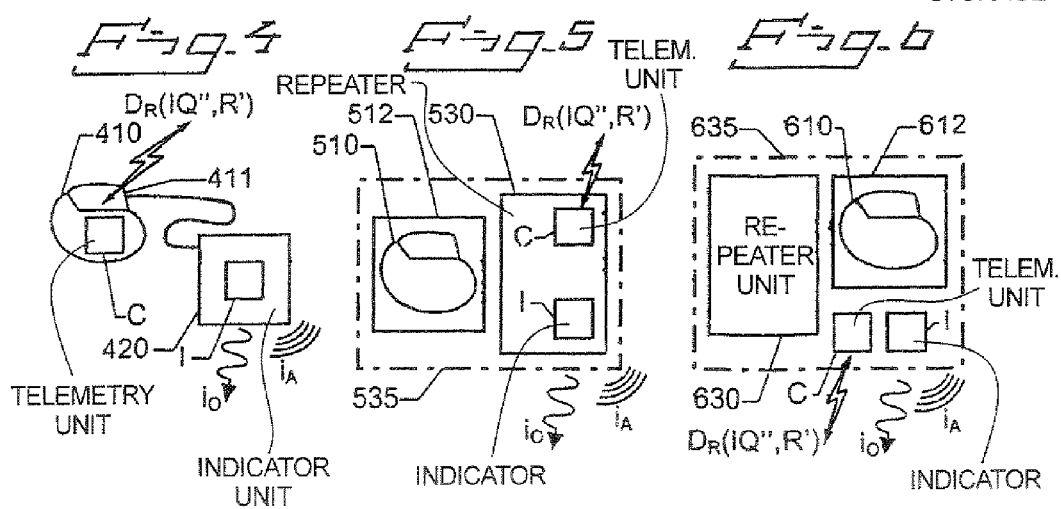

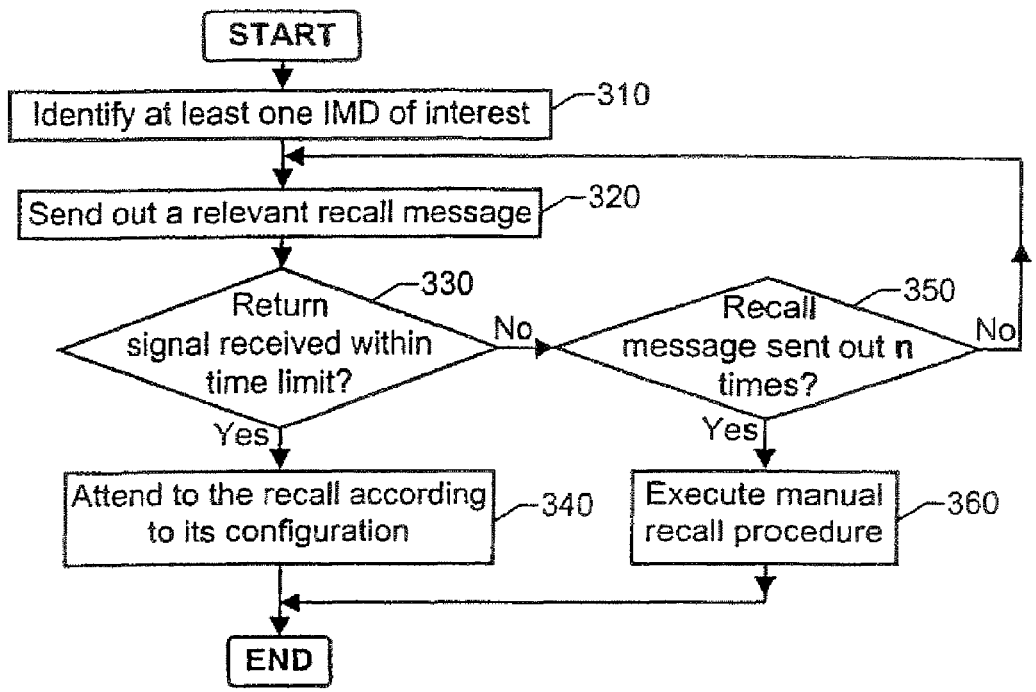
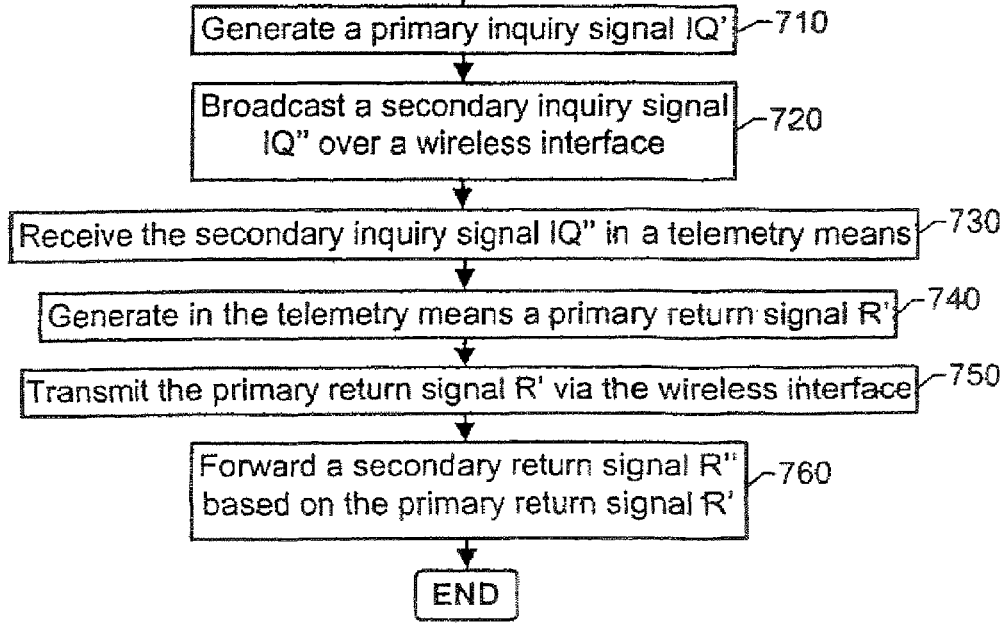

MANAGEMENT OF IMPLANTABLE DEVICES

BACKGROUND OF THE INVENTION

1. Field of the Invention

The present invention relates generally to implantable medical devices that are associated with telemetry means for wireless data exchange with external units. More particularly the invention relates to a method for organizing not yet implanted implantable medical devices as well as a computer program, a computer readable medium, a system and a local administration unit for implanting such a method.

2. Description of the Prior Art

In recent years the processing and data storage capacity of implantable medical devices (IMD), such as pacemakers, has increased dramatically. Following this advancement, techniques for interacting with these kinds of devices has likewise been developed. Today, a broad spectrum of different systems are known for supervising and re-programming implanted medical devices over various kinds of communication networks.

FIG. 1 illustrates a typical structure for such a system. A medical device 110 having a telemetry unit is here presumed to be implanted into a patient 115. The device 110 is able to exchange data DR with a repeater unit 130 via a wireless channel 120, which is set up between the telemetry unit in the repeater unit 130 over the network 140. The repeater unit 130, in turn, has a network interface 140a to a communications network 140. An external unit 150, e.g. a remote programmer, also has a network interface 140b to the network 140 and may thus communicate with the repeater unit 130. This, in combination with the wireless channel 120, accomplishes a chain of communication between the external unit 150 and the device 110, which preferably is bi-directional. Classically, measurement data is sent from the device 110 to the external unit 150, while control commands, parameter settings and/or re-programming code is transmitted in the reverse direction. In most cases, the external unit 150 is linked to a memory 160 including at least a patient database. The characteristics of the device 110 and mode of operation can thereby be adjusted, for example based on historical measurement data from the device 110, which has been loaded into the memory 160 earlier.

U.S. Pat. No. 6,249,705 discloses a distributed network system for use with IMDs, which enables a multitude of programmers to communicate with a specific IMD. A network server allows each programmer to exploit a far greater amount of processing power than a stand-alone programmer. Moreover, a database linked to the network server provides easy information access to the physicians as well as a basis for software updates of the IMDs.

U.S. Pat. No. 6,292,698 discloses a worldwide patient location and data telemetry system for IMDs through which the function of the devices may be selectively monitored. Telemetry data may be transmitted via a satellite network, a landline telephone network or a cellular telephone network.

Published U.S. patent application Ser. No. 20010031997 describes a data communication system, which permits collaboration between distributed clinicians regarding distributed or remote IMDs. By means of the system, an implanted medical device may be polled by an interface device external to the host patient and data may be transmitted to the interface device through wireless communication. This data may then be sent to a central computer for storage and further distribution.

PCT Application WO01/82210 describes a component architecture for medical devices system networks, which are intended to administer implanted medical devices over at least one network, such as the internet. The proposed system enables a central computing resource to exchange data with a particular medical device that is implanted into the body of a patient. Naturally, the existence of the device in question inside the body is here presumed to be known beforehand. Moreover, before initiating the data exchange, the patient must position himself/herself within communication range of a network interface that is adapted to communicate with the implanted device.

Thus, the prior art includes many examples of solutions for remote supervising and re-programming of implanted medical devices but there is no solution for administrating IMDs. Therefore, all administrative procedures with respect of devices in this category must be effected on a manual basis, which in many cases can be both resource and time consuming. For instance, if a recall of devices becomes necessary, this typically affects only not yet to be implanted devices. Still, locating each relevant device could prove to be a very complex task, particularly since a given batch of devices may be distributed to a large number of retailers and hospitals around the globe.

Other problems are billing and stock tracking, i.e. maintaining an up-to-date inventory of devices currently in stock, either at the manufacturer or at a retailer.

Furthermore, in emergency situations it may be critical to quickly find a suitable IMD for a specific patient. A large local stock (at e.g. a hospital), which includes a wide variety of products here poses an additional problem.

SUMMARY OF THE INVENTION

It is an object of the present invention to alleviate the problems noted above and thus to provide an improved solution for organizing not yet implanted IMDs.

The above object is achieved in accordance with the invention a method of organizing not yet implanted IMDs, where each IMD is presumed to be associated with a respective telemetry unit for wireless exchange of data with a remote external unit. The method includes communicating at least one inquiry signal and at least one return signal over a wireless interface between at least one telemetry unit and a local administration unit. Specifically, these signals establish the existence of at least one implantable medical device. The method also includes matching registered device identities against information contained in an inquiry signal, and determining a course of action to be taken with respect to at least one implantable medical device based on the result of the matching.

An important advantage attained by this procedure is that the remote external unit is able to automatically administrate not yet implanted IMDs. For example, a total number of devices of a particular model and version in stock can be effortlessly acquired. Moreover, in case of a recall situation, the inquiry signal may include a recall message and the at least one return signal may include identifications specifying the locations of any not yet implanted devices that should be recalled. Thereby, an automated recall procedure is supported.

According to a preferred embodiment of the method of the invention, the method further includes generating a primary inquiry signal in the remote external unit and broadcasting a secondary inquiry signal over a wireless interface. The secondary inquiry signal is based on the primary inquiry signal. Moreover, the method includes receiving, via the wireless interface, the secondary inquiry signal in at least one telemetry unit and generating, in response to the secondary inquiry signal, a respective primary return signal in each telemetry unit, which are associated with a device that fulfills a requirement specified in the secondary inquiry signal. Additionally, the method includes transmitting, via the wireless interface, the (at least one) primary return signal from the at least one telemetry unit and forwarding, to the remote external unit, a secondary return signal being based on the primary return signal.

This procedure is advantageous because it makes it possible to adapt the signal formats to the relevant transmission media. Furthermore, an aggregated secondary return signal may be generated, which is based on two or more primary return signals.

According to a preferred embodiment of this aspect of the invention, the method involves retrieving device data that pertains to at least one IMID from a first central data storage, and generating the primary inquiry signal on basis of this device data. Thereby, automated recall and stocktaking procedures are further supported.

According to a preferred embodiment of the method of the invention, the method includes entering patient data that indicate at least one patient specific parameter with respect to a potential user of an IMD, and generating the primary inquiry signal on basis of the patient data, possibly in combination with the device data. Thereby, procedures for finding a unit most suitable for a specific patient are supported, which is advantageous in many situations. Preferably, the patient data are retrieved from a second central data storage.

The above object also is achieved in accordance with the invention by a computer program directly loadable into the internal memory of a digital computer, having software for controlling the method described above when the program is run on the computer.

The above object also is achieved in accordance with the invention by a computer readable medium, having a program recorded thereon, wherein the program is for the purpose of causing a computer perform the method described above.

The above object also is achieved in accordance with the invention by a system for organizing not yet implanted IMDs, wherein each IMD is associated with a respective telemetry unit for wireless exchange of data with a remote external unit. The system includes a local administration unit, which is adapted to communicate at least one inquiry signal and at least one return signal with at least one telemetry unit over a wireless interface, establish the existence of at least one implantable medical device, and match registered device identities against information contained in an inquiry. The system also includes at least one remote external unit that has a network connection to the local administration unit and is adapted to determine a course of action to be taken in respect of at least one implantable medical device based on the result of a matching performed by the local administration unit.

Such system is advantageous, since it allows the remote external unit to automatically administrate the not yet implanted IMDs, for instance, when taking inventory, or for billing or when a recalling devices.

According to a preferred embodiment of the system of the invention, the system includes a first central data storage, which contains device data pertaining to at least one IMD. Moreover, the system contains a first remote external unit adapted to retrieve device data from the first central data storage and on basis thereof generate a primary inquiry signal, and receive and process a secondary return signal. The local administration unit within the system is adapted to receive the primary inquiry signal and on basis thereof generate a secondary inquiry signal. The local administration unit is also adapted to broadcast the secondary inquiry signal over the wireless interface and receive at least one primary return signal over this interface. Additionally, the system includes at least one telemetry unit adapted to receive the secondary inquiry signal via the wireless interface, and in response thereto generate a primary return signal. Moreover, the (at least one) telemetry unit is adapted to transmit the primary return signal over the wireless interface. Thereby, an aggregated secondary return signal may be generated, which is based on two or more primary return signals. The signal formats may also be adapted to the relevant transmission media, which of course is desirable.

According to a preferred embodiment of the system of the invention, at least one first IMD includes a telemetry unit, which is adapted to receive the secondary inquiry signal, and in response thereto, to generate a primary return signal. The telemetry unit is also adapted to transmit the primary return signal over the wireless interface. This embodiment is advantageous, since it allows a direct communication with the IMD.

According to a preferred embodiment of the system of the invention, at least one second IMD is associated with a repeater unit. This unit also includes a telemetry unit, which is adapted to receive the secondary inquiry signal, and in response thereto, to generate a primary return signal. The telemetry unit is also adapted to transmit the primary return signal over the wireless interface. The embodiment is advantageous, since it does not require a usage of the energy resources in the IMD.

According to a preferred embodiment of the system of the invention, at least one third IMD is associated with a device box. This box, also includes a telemetry unit, which is adapted to receive the secondary inquiry signal, and in response thereto, to generate the primary return signal. The telemetry unit is also adapted to transmit the primary return signal over the wireless interface. The embodiment is advantageous, since it will not consume energy resources in the IMD nor in its repeater unit.

According to preferred embodiments of the above-described versions of the invention, the first IMD is connected to an indicator, the repeater unit contains an indicator and the device box includes an indicator. This indicator is adapted to produce a local indication signal (e.g. optical and/or acoustic) in connection with the generation of the primary return signal. These embodiments are advantageous, since they all facilitate the physical location of a relevant device.

The above object also is achieved in accordance with the invention by a local administration unit for communicating administrative signals pertaining to organization of not yet implanted IMDs of which each is associated with a respective telemetry unit. The local administration unit contains at least one network interface and a wireless interface. The at least one network interface is adapted to receive at least one first inquiry signal from a remote external unit and transmit a second return signal to the remote external unit. The wireless interface is adapted to establish the existence of at least one implantable medical device by means of a transmitted second inquiry signal based on the first inquiry signal and at least one received first return signal, which is produced by at least one telemetry unit in response to the second inquiry signal. Furthermore, the local administration unit is adapted to match registered device identities against information contained in the first and second inquiry signals, and produce, based on the result of the matching, the second return signal to form a basis for a course of action to be taken in respect of at least one implantable medical device.

The inventive local administration unit is advantageous, since it represents a link, which enables administration of distributed unimplanted IMDs from a central point. Although the inventive solution is primarily intended for cardiac devices; such as pacemakers and defibrillators, the invention is equally applicable to any alternative type of IMDs, for example drug pumps or neurostimulators.

BRIEF DESCRIPTION OF THE DRAWINGS

FIG. 1 shows a prior art system for remote communication with an IMD.

FIG. 2 shows a system for organizing not yet implanted IMDs according to an embodiment of the invention.

FIG. 3 is a flowchart illustrating a method for performing a recall procedure of not yet implanted IMDs according to an embodiment of the invention.

FIG. 4 shows a not yet implanted IMD connected to an indicator unit according to an embodiment of the invention.

FIG. 5 shows a not yet implanted IMD associated with a repeater unit having an indicator according to a further embodiment of the invention.

FIG. 6 shows a not yet implanted IMD associated with a repeated unit having an indicator according to a further embodiment of the invention.

FIG. 7 is a flowchart for a method for organizing not yet implant IMDs according to an embodiment of the invention.

DESCRIPTION OF THE PREFERRED EMBODIMENTS

FIG. 2 shows a system for organizing not yet implanted IMDs 210a, 210b and 210c respectively according to an embodiment of the invention. Each of the IMDs 210a, 210b and 210c are associated with a respective telemetry unit for wireless data communication. A local administration unit 237 is positioned within the communication ranges of the telemetry units of the IMDs 210a, 210b and 210c, i.e. relatively proximate to the devices. The local administration unit 237 may thus communicate with the IMDs 210a, 210b and 210c over a wireless interface 220a, 220b and 220c to their respective telemetry units. Preferably, the IMDs 210a, 210b and 210c are gathered in a storage area S at, for example a manufacturer M, a hospital H or a retailer. Depending on various conditions (such as type, model, version, buyer preferences etc.) the devices 210a, 210b and 210c may be packaged differently. Here, a first device 210a is packaged in a first device box 235a together with an associated first repeater unit 230a, correspondingly a second device 210b is packaged in a second device box 235b together with an associated second repeater unit 230b while a third device 210c is packaged in a third device box 235c without an associated repeater unit.

The local administration unit 237 has a network interface 240a, to a communications network 240, e.g. the Internet, a PSTN (Public Switched Telephone Network) or equivalent. Hence, the unit 237 may be identified in the network 240 by means of a unique identifier, such as an IP-address or a telephone number.

A first remote external unit 270 has a network interface 240c towards the communications network 240, either directly or via at least one other network. In analogy to the local administration unit 237, the first remote external unit 270 has a unique identifier through which it may be addressed by other units having access to the network 240. Consequently, a connection may be established between the first remote external unit 270 and the local administration unit 237 over the network 240. Due to the wireless interface 220a, 220b and 220c, communication can also be accomplished between the first remote external unit 270 and the respective telemetry units associated with the IMDs 210a, 210b and 210c. Particularly, the first remote external unit 270 may generate a primary inquiry signal IQ', which is passed on to the local administration unit 237. This unit 237 then converts the primary inquiry signal IQ' into a at least one secondary inquiry signal IQ", which is adapted to the signal format of the wireless interface 220a, 220b and 220c. The secondary inquiry signal IQ" is broadcast over the wireless interface 220a, 220b and 220c for intended reception at the IMDs 210a, 210b and 210c.

According to a preferred embodiment of the invention, the telemetry units associated with the IMDs 210a, 210b and 210c generate a respective primary return signal R' in response to the secondary inquiry signal IQ", at least for those devices that fulfill a requirement specified in the secondary inquiry signal. This requirement may, for instance, imply matching the device's identity with the contents of a recall message. Alternatively, the requirement may relate to a stock inquiry or a billing operation. In addition to one or more device identities, the recall message may include information pertaining to advisory actions, notifications and upgrading. According to another preferred embodiment of the invention, any telemetry unit receiving the secondary inquiry signal IQ" shall reply with a respective primary return signal R', irrespective of whether the secondary inquiry signal IQ" pertains to the corresponding implantable device or not.

In any case, one or more primary return signals R' may be sent via the wireless interface to the local administration unit 237 in response to the secondary inquiry signal IQ". Preferably, the local administration unit 237 aggregates any received primary return signals R" into a joint message, which is sent in the form of a secondary return signal R" to the first remote external unit 270 over the communications network 240. However, each received primary return signal R' may equally well be transformed into a particular secondary return signal R", which are forwarded separately to the first remote external unit 270. Based on the at least one secondary return signal R", the first remote external unit 270 determines a further course of action, such as generating an invoice (in the billing-case) or producing a return instruction (in the recall-case).

According to a preferred embodiment of the invention, the first remote external unit 270 has access to a first central data storage 275, which contains device data $D_d$ pertaining to at least one of the IMDs 210a, 210b and 210c. The first remote external unit 270 may thus retrieve device data $D_d$ from the first central data store 275 and generate the primary inquiry signal IQ' based on this data $D_d$. Typically, the device data $D_d$ includes the following information for each IMD: a device identity (e.g. a serial number), a batch number, a model designation, a version designation, a date of production and a latest registered location of the device.

According to a preferred embodiment of the invention, the primary inquiry signal IQ' is generated on basis of patient data $D_p$, i.e. information pertaining to patient specific parameters, such as previous medical condition, age, etc. The patient data $D_p$ may either be entered on a completely manual basis or at least partially be retrieved from a second central data store 255 and be fed into a second remote external unit 250. Analogous to the first remote external unit 270, the second remote external unit 250 has a network interface 240b towards the communications network 240, either directly or via at least one other network. In most cases, the patient data $D_p$ is entered via a particular hospital or clinic. Moreover, the patient data $D_p$ is relevant to a physician practicing at this medical unit when deciding to implant a certain IMD. Therefore, the second remote external unit 250 and the second central data store 255 are preferably both located in a hospital area H. For instance, in an emergency situation, the physician may consult the second central data store 255 to obtain a recommendation of a suitable device for his/her patient. Given the patient data $D_p$, the second remote external unit 250 sends out a primary inquiry signal IQ' to at least one local administration unit 237 in proximity of a stock of IMDs being relatively readily accessible to the physician. Based on a corresponding secondary return signal R", the second remote external unit 250 recommends a suitable IMD in stock (provided, of course, that such device exists). Either the primary inquiry signal IQ' is exclusively based on the patient data $D_p$ or this signal IQ' also contains device data $D_d$ from the first central data store 275.

Preferably, the necessary data is exchanged between the first remote external unit 270 and the second remote external unit 250 via the communications network 240. However, a direct connection for this purpose may also be set up between the units 250 and 270. For instance, data $D_d$ pertaining to a recall instruction may be sent via such connection from the first remote external unit 270 to the second remote external unit 250.

FIG. 3 illustrates, by means of a flow diagram, a method of performing a recall procedure with respect to one or more not yet implanted IMDs according to an embodiment of the invention. A first step 310 presumes that the manufacturer has become aware of an imperfection in, for example a batch of IMDs. Expiration of a latest recommended implantation date represents a typical example of such imperfection. Namely, due to the chemical constituents of the batteries in an IMD, the device should be implanted before the chemical aging process has reached a certain stage in order to guarantee a stated lifetime for the device. The concerned devices are thus identified as candidates for a recall. In most cases when a recall proves necessary, this only affects those devices that have not yet been implanted into a patient. Due to the extremely rigorous safety regulations governing the IMD industry, the imperfections of a device that may be found after delivery are very seldom severe enough to justify explantation, i.e. be prone to cause immediate health risks for the patient. Typically, a follow-up examination is instead held earlier than originally planned in order to compensate for the imperfection. Today, a lower than expected battery capacity is one of the most common defects that are encountered after delivery of a device. This problem is rarely a ground for performing an immediate explantation of the device.

However if possible, implantation of a not yet implanted imperfect device should certainly be avoided. To this aim, a relevant recall message is sent out in a step 320. As mentioned above, the recall message may be included in a primary inquiry signal IQ' and a secondary inquiry signal IQ" sent out from the remote external units 250 and/or 270 and the local administration unit 237 respectively.

A subsequent step 330, investigates whether a return signal has been received (i.e. a secondary return signal R" has been received in either or both of the units 250 and 270) within a predetermined time limit, and if so, the procedure continues to a step 340. Otherwise, a step 350 investigates whether the recall message has been sent out a predetermined number of times n (where n is an integer>1). If the question posed in the step 350 is answered in the negative, the procedure loops back to the step 320 again. Otherwise, a step 360 is entered, which involves a manual recall operation. I.e. the proposed procedure has here failed to reach the relevant devices, possibly because all of them have already been implanted into patients.

In the step 340 however, an automatic recall procedure is initiated. This may involve transmitting a disable message or an instruction to a responsible clinician, which requests him/her to discard the concerned device(s) respective return it(them) to the manufacturer. Nevertheless, also this procedure normally includes various manual steps and measures before the recall is entirely completed.

FIG. 4 shows a not yet implanted IMD 410, which is connected to an indicator unit 420 according to a first alternative embodiment of the invention. The IMD 410 contains a telemetry unit C for exchange of data $D_R$ (IQ", R') with external units via a wireless interface. The IMD 410 may thus receive a secondary inquiry signal IQ" and transmit a primary return signal R'. Preferably, a sterile packing (not shown) surrounds both the device 410 and the indicator unit 420.

An indicator I in the indicator unit 420 is adapted to produce a local indication signal $i_O$, $i_A$ in connection with the generation of the primary return signal R', such that the process of physically locating the device is facilitated. Preferably, the local indication signal is either an optical signal $i_O$, (e.g. produced by a light emitting diode, LED), an acoustic signal $i_A$ (produced by a buzzer or similar) or a combination thereof. According to a preferred embodiment of the invention, the indicator unit 420 is connected to the IMD 410 via a cable to an electrode connector in the device 410.

FIG. 5 shows a not yet implanted IMD 510, which is associated with a repeater unit 530 having an indicator I according to a second alternative embodiment of the invention in order to facilitate location of the device. Preferably, a sterile packing 512 surrounds at least the device 510. The IMD 510 and the repeater unit 530 are placed in a common device box 535. The repeater unit 530 is here equipped with a telemetry unit C for exchange of data $D_R$(IQ", R') with external units via a wireless interface. The IMD 510 may thus receive a secondary inquiry signal IQ" and transmit a primary return signal R' via the repeater unit 530. By positioning the telemetry unit C outside the device 510, the energy resources therein are economized.

The indicator I is adapted to produce a local indication signal $i_O$, $i_A$ in connection with the generation of the primary return signal R', either in the form of an optical signal $i_O$, (e.g. produced by a light emitting diode, LED), an acoustic signal $i_A$ (produced by a buzzer or similar) or a combination thereof.

FIG. 6 shows a not yet implanted IMD 610, which in similarity with the device 510 above, is associated with a repeater unit 630 together with which it is placed in a device box 635. A sterile packing 612 surrounds the device 610, however not necessarily the repeater unit 630. Here, however, the box 635 itself includes a telemetry unit C for exchange of data $D_R$(IQ", R') with external units via a wireless interface. The IMD 610 may thus receive a secondary inquiry signal IQ" and transmit a primary return signal R' via the device box 635. Naturally, by positioning the telemetry unit C outside both the device 610 and the repeater unit 635, the energy resources in both these units are economized.

The device box 635 also includes an indicator 1, which is adapted to produce a local indication signal $i_O$, $i_A$ in connection with the generation of the primary return signal R', either in the form of an optical signal $i_O$, (e.g. produced by a light emitting diode, LED), an acoustic signal $i_A$ (produced by a buzzer or similar) or a combination thereof.

In summary, the general method of organizing not yet implanted IMDs according to the invention will now be described with reference to FIG. 7.

A first step 710 involves generating a primary inquiry signal IQ' in an originating remote external unit. Then, a secondary inquiry signal IQ" is broadcast in a step 720 over a wireless interface to a multitude of not yet implanted IMDs. Subsequently, a step 730 receives the secondary inquiry signal IQ" and a following step 740 generates a primary return signal R' in response thereto. The primary return signal R' is generated in at least one telemetry means that is associated with the IMDs. After that, a step 750 transmits the at least one primary return signal 'R' over the wireless interface. Finally, a step 760 forwards a secondary return signal R", based on the primary return signal R', to the originating remote external unit.

All of the process steps, as well as any sub-sequence of steps, described with reference to FIG. 7 above may be controlled by means of a computer program being directly loadable into the internal memory of a computer, which includes appropriate software for controlling the necessary steps when the program is run on a computer. Furthermore, such computer programs can be recorded onto arbitrary kind of computer readable medium as well as be transmitted over arbitrary type of network and transmission medium.

Although modifications and changes may be suggested by those skilled in the art, it is the invention of the inventors to embody within the patent warranted heron all changes and modifications as reasonably and properly come within the scope of their contribution to the art.

The invention claimed is:

1. A method for organizing not yet implanted implantable medical devices each having a telemetry unit associated therewith, comprising the steps of:
   wirelessly transmitting a first inquiry signal from a local administration unit to the telemetry unit associated with one of said not yet implanted medical devices;
   wirelessly transmitting a return signal, in response to said first inquiry signal, from said telemetry unit of said one of said not yet implanted medical devices to said local administration unit and thereby informing said local administration unit of the existence of said one of said not yet implanted medical devices;
   supplying a second inquiry signal to said local administration unit containing identity information for a not yet implanted implantable medical device;
   in said local administration unit, matching said identity information in said second inquiry signal with an identity of said at least one not yet implanted medical device; and
   determining a pre-implantation action to be taken for said one of said medical devices as a result of said matching.

2. A method as claimed in claim 1 comprising:
   generating said second inquiry signal in an external unit remote from said local administration unit and including an inquiry requirement in said second inquiry signal, and supplying said second inquiry signal from said external unit to said local administration unit;
   in said local administration unit, generating said first inquiry signal dependent on said second inquiry signal, and including said inquiry requirement in said first inquiry signal;
   in said return signal, including a response to said inquiry requirement; and
   forwarding said response to said inquiry requirement from said local administration unit to said external unit.

3. A method as claimed in claim 2 comprising:
   storing device data for each of a plurality of not yet implanted implantable medical devices in a central data storage accessible by said external unit; and
   generating said second inquiry signal in said external unit dependent on said device data for one of said not yet implanted medical devices.

4. A method as claimed in claim 2 comprising:
   entering patient data into said external unit designating a patient specific parameter for a candidate patient of a not yet implanted implantable medical device; and
   generating said second inquiry signal in said external unit dependent on said patient data.

5. A method as claimed in claim 4 wherein the step of entering said patient data comprises storing patient data for a plurality of patients in a central data storage accessible by said external unit, and retrieving patient data for said candidate patient from said central data storage.

6. A method as claimed in claim 2 comprising generating said second inquiry signal in said external unit as a part of a recall procedure for said one not yet implanted medical device.

7. A method as claimed in claim 2 comprising generating said second inquiry signal in said external unit as a part of a invoicing procedure for said one not yet implanted medical device.

8. A computer readable medium encoded with a data structure for organizing not yet implanted implantable medical devices each having a telemetry unit associated therewith, said data structure programming a local administration unit to:
   wirelessly transmit a first inquiry signal from the local administration unit to the telemetry unit associated with one of said not yet implanted medical devices;
   wirelessly receive a return signal, in response to said first inquiry signal, from said telemetry unit of said one of said medical devices at said local administration unit and thereby informing said local administration unit of the existence of said one of said not yet implanted medical devices;
   receive a second inquiry signal at said local administration unit containing identity information for a not yet implanted implantable medical device;
   match said identification unit in said second inquiry signal with an identity of said at least one not yet implanted medical device; and
   determine a pre-implantation action to be taken for said one of said not yet implanted medical devices as a result of said matching.

9. A system for organizing not yet implanted implantable medical devices, comprising:
   a plurality of not yet implanted implantable medical devices, each having a telemetry unit associated therewith;
   a local administration unit having a wireless interface for communicating with each of said telemetry units, said local administration unit wirelessly transmitting a first inquiry signal to one of said medical devices via the telemetry unit associated therewith, and receiving a return signal in response thereto from said one of said not yet implanted medical devices, thereby establishing existence of said one of said not yet implanted medical devices in said local administration unit;

a remote external unit in communication with said local administration unit, said external unit communicating a second inquiry signal from said external unit to said local administration unit containing identity information for a not yet implanted medical device;

said local administration unit matching said identity information to said existence of said one of said not yet implanted medical devices; and said external unit determining a pre-implantation action to be taken for said one of said not yet implanted medical devices dependent on said matching in said local administration unit.

10. A system as claimed in claim 9 comprising:
a central data storage, accessible by said external unit, containing device data for a plurality of not yet implanted medical devices;

said external unit retrieving said device data from said central data storage and including said device data in said second inquiry signal;

said local administration unit generating said first inquiry signal dependent on said device data in said second inquiry signal and generating a further return signal, dependent on said return signal from said telemetry unit associated with said one of said not yet implanted medical devices, and communicating said further return signal to said external unit.

11. A system as claimed in claim 10 wherein said telemetry unit is contained in said one of said medical devices.

12. A system as claimed in claim 10 comprising an indicator unit connected to said one of said not yet implanted medical devices, said indicator unit generating a local indication signal upon generation of said return signal.

13. A system as claimed in claim 10 comprising a repeater unit, containing said telemetry unit, associated with said one of said not yet implanted medical devices, said repeater unit receiving said first inquiry signal and generating said return signal in response thereto and transmitting said return signal via said telemetry unit.

14. A system as claimed in claim 13 wherein said repeater unit comprises an indicator for generating a local indication signal upon generation of said return signal.

15. A system as claimed in claim 9 comprising a device package for said one of said not yet implanted medical devices, said device package containing said telemetry unit associated with said one of said not yet implanted medical devices.

16. A system as claimed in claim 15 wherein said device package comprises an indicator for generating a local indication signal upon generation of said return signal.

17. A local administration unit for communicating administrative signals pertaining to organization of not yet implanted implantable medical devices, each of said medical devices having a telemetry unit associated therewith, said local administration unit comprising:

a network interface adapted to receive an inquiry signal from a remote external unit;

a signal generator for generating a further inquiry signal dependent on said inquiry signal;

a wireless interface adapted for wireless communication with at least one of said telemetry units for communicating said further inquiry signal thereto and for receiving a return signal therefrom in response thereto;

a matching unit for matching registered device identities for respective not yet implanted medical devices against information contained in said inquiry signal and said further inquiry signal; and said signal generator generating a further return signal dependent on said matching forming a basis for a pre-implantable course of action to be taken for the not yet implanted medical device from which the return signal was received.

18. A local administration unit as claimed in claim 17 wherein said wireless interface broadcasts said further inquiry signal to a plurality of telemetry units respectively associated with a plurality of not yet implanted medical devices.

19. A local administration unit as claimed in claim 18 comprising a network interface adapted to communicate said inquiry signal and said further return signal via a communication network.

* * * * *